United States Patent [19]

Matsuo

[11] 4,455,963

[45] Jun. 26, 1984

[54] HAND SIMULATOR

[76] Inventor: Masayuki Matsuo, No. 4-21-3, Gyotoku-Ekimae, Chiba-shi, Chiba-Prefecture, Japan

[21] Appl. No.: 379,967

[22] Filed: May 19, 1982

[30] Foreign Application Priority Data

Mar. 1, 1982 [JP] Japan .............................. 57-28721[U]

[51] Int. Cl.³ .............................................. G09F 9/00
[52] U.S. Cl. ...................................... 116/306; 116/200; 116/307; D2/360; D2/361; D20/33; 446/26
[58] Field of Search ............... 116/200, 222, 306, 307, 116/35 R; 273/166, DIG. 26; 46/163; 272/1 R, 8 N; 434/205; 2/161 A, 163, 168; D2/376, 360, 361; D11/104; D20/30

[56] References Cited

U.S. PATENT DOCUMENTS

| 249,400 | 9/1978 | Pearson | D11/104 |
| 258,860 | 4/1981 | DiPietro | D11/104 |
| 925,207 | 6/1909 | Lindner | 2/163 |
| 1,149,139 | 8/1915 | Heagle | D2/361 |
| 3,740,766 | 6/1973 | Kobylarz | 2/161 A |

FOREIGN PATENT DOCUMENTS

| 527868 | 6/1955 | Italy | D11/104 |
| 536978 | 12/1955 | Italy | 116/35 |

Primary Examiner—Charles Frankfort
Assistant Examiner—David R. Schuster
Attorney, Agent, or Firm—Pearne, Gordon, Sessions, McCoy, Granger & Tilberry

[57] ABSTRACT

This invention relates to a hand simulator usable for hand sign or signal. The hand simulator comprises a palm portion of cushiony material and five finger portions of cushiony material integrally extending from the palm portion. The five finger portions are normally extended and spaced at their finger tips. The palm portion has a plurality of holes provided therein. The finger portions are selectively inserted into the corresponding holes to give a manual sign or signal.

9 Claims, 4 Drawing Figures

HAND SIMULATOR

BACKGROUND OF THE INVENTION

In various games such as baseball, soccer and football, for example, which are to be held in relatively larger studiums, a cheering contest is actively made. In such a case, the cheering party often manually gives a V-signal (Victory signal), for example. However, since a genuine hand is too small, the signal is never conspicuous. Otherwise, a man or woman is sometimes required to put a mark thereon in the crowd. In the prior art, there has been no article which can conspicuously give a signal or a mark.

SUMMARY OF THE INVENTION

Accordingly, it is a principal object of the invention to provide a hand simulator usable for hand sign or signal.

It is another object of the invention to provide a hand simulator which can be easily handled with a small weight.

In accordance with the invention, there is provided a hand simulator comprising a palm portion of cushiony material and five finger portions of cushiony material integrally extending from said palm portion and being normally extended and spaced at their tips from each other, and said palm portion having a plurality of holes provided therein whereby said finger portions are to be selectively inserted into said holes.

BRIEF DESCRIPTION OF THE DRAWING

The above and other objects and features of the invention will be apparent from the description of the embodiment taken with reference to the accompanying drawing in which.

DETAILED DESCRIPTION OF THE EMBODIMENT

Figure 1:
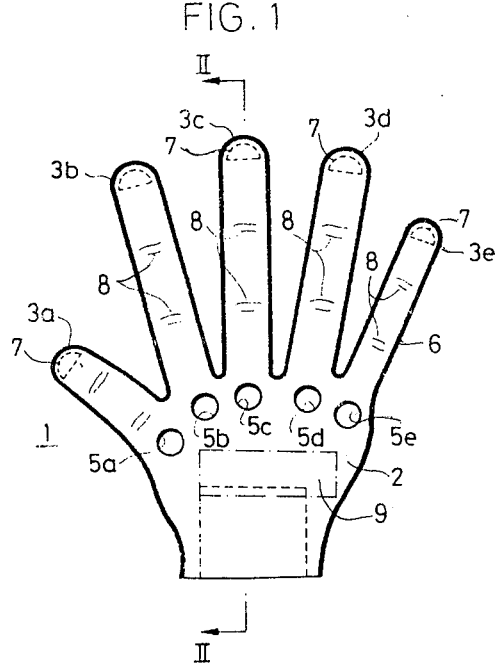
FIG. 1 is a front view of a hand simulator constructed in accordance with the embodiment of the invention.
Figure 2:
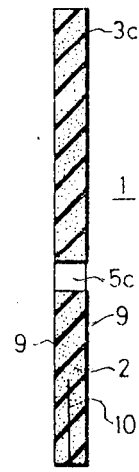
FIG. 2 is a cross sectional view of the hand simulator taken along the line 11—11 of FIG. 1.

Referring now to FIGS. 1 and 2, there is shown a hand simulator 1 which comprises a palm portion 2 and five finger portions 3a, 3b, 3c, 3d and 3e integrally extending from the palm portion 2. The finger portions 3a, 3b, 3c, 3d and 3e correspond to a thumb, a forefinger, a middle finger, a third finger and a little finger, respectively. The palm portion 1 and the five finger portions 3a, 3b, 3c, 3d and 3e are formed of cushiony plastic material such as foamed urethane having a resilience and a small weight. They may be formed by blanking a cushiony sheet of predetermined thickness.

A plurality of holes are provided in the palm portion 2 near its top where the five finger portions are integrally connected. In the illustrated embodiment, five holes 5a, 5b, 5c, 5d and 5e may be provided corresponding to the five finger portions 3a, 3b, 3c, 3d and 3e, respectively. The holes may preferably have a size smaller than those of the tips of the finger portions 3a, 3b, 3c, 3d and 3e. A margin 6 may be preferably formed by printing, for example, on the front and back faces of the hand simulator 1 so that the peripheries of the palm portion 2 and the five finger portions 3a through 3e can be noticeably seen from far away. Nails 7 and joints 8 may be indicated by printing, for example, on inner faces of the five finger portions 3a through 3e. Also, an indication face portion 9 may be formed on both faces of the palm portion 2 so that various indications such as a name, a symbol, a cheering word or words and a name of school, for example may be made.

As noted from FIG. 2, a split 10 extending from the lower edge of the palm portion 2 may be formed into which a hand of a user can be inserted to hold the hand simulator.

Although, in the illustrated embodiment, the left hand simulator is illustrated, the invention may be applied to the right hand simulator. In this case, it may be formed by printing the nails 7, the joints 8 and the indication face portion 9 on the back face of the blank. Also, although the five holes 5a through 5e may be provided in the palm portion 2, two, three or four holes may be provided in the palm portion 2 because two or three finger tips can be inserted into one of the holes. It will be understood that the holes may be provided in the palm portion 2 at other positions.

Figure 3:
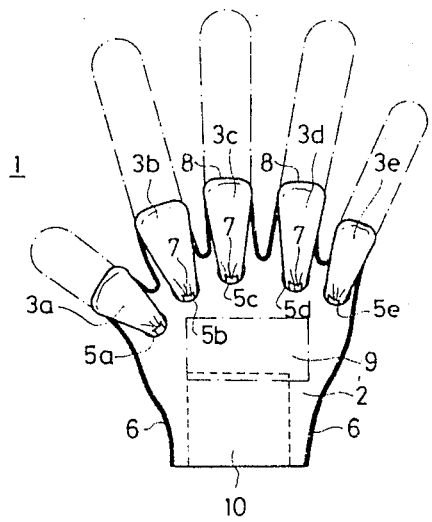
FIGS. 3 and 4 illustrate how the hand simulator is to be used.

The hand simulator 1 is normally kept so that the finger portions are extended and spaced from each other as shown in FIG. 1. FIG. 3 shows that all the finger portions 3a through 3e are bent and at their tips inserted into the corresponding holes 5a through 5e in the palm portion 2. It will be noted that this indicates "stone" at a mora. If the two finger portions 3b and 3c are bent and inserted into the holes 5b and 5c, then this will indicate "scissors" at the mora. If all the finger portions 3a through 3e are extended as shown in FIG. 1, then this will illustrate "paper" at the mora. In case that some or all of the finger portions are inserted into the corresponding holes, they are prevented from being removed out of the corresponding holes because the resistance of the finger tips to the hole walls is greater than their power of restitution. In this manner, it will be understood that children can play a game of mora by using the hand simulator of the invention and that it can be easily handled because it is relatively light.

Figure 4:
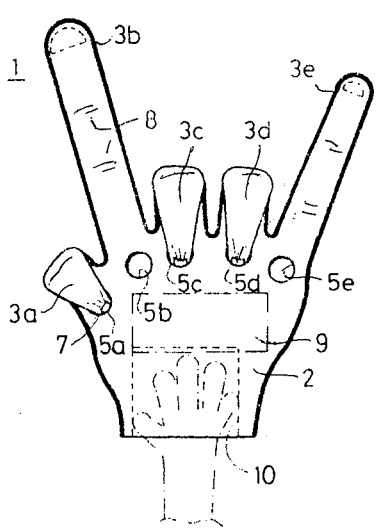

FIG. 4 shows that the hand simulator 1 indicates a V-sign. This can be accomplished by bending and inserting the finger portions 3a, 3c and 3d into the corresponding holes 5a, 5c and 5d while the other finger portions 3b and 3e are extended. It should be noted that any of the finger portions 3a through 3e may be bent and inserted into the corresponding hole or holes so as to give any suitable signal.

The hand simulator 1 may be used for a cushion on which a user sits or for an ornament when it is not used for hand sign or signal.

Although one preferred embodiment of the invention has been described and illustrated with reference to the accompanying drawing, it will be understood by those skilled in the art that it is by way of example and that various changes and modifications may be made without departing from the spirit and scope of the invention, which is intended to be defined only by the appended claims.

What is claimed is:

1. A hand simulator comprising a palm portion of cushiony material and five finger portions of cushiony material integrally extending from said palm portion and being normally extended and spaced at their finger tips from each other, said palm portion and finger portions being substantially larger than any human hand, and said palm portion having a plurality of holes provided therein extending completely through the thickness of the hand simulator whereby said finger portions are to be selectively inserted into said holes.

2. A hand simulator as set forth in claim 1, and further comprising a split longitudinally extending into said palm portion from the lower edge of said palm portion whereby a hand of a user is to be inserted into said split.

3. A hand simulator as set forth in claim 1, and further comprising nail and joint indications provided on the faces of said five finger portions.

4. A hand simulator as set forth in claim 1, and further comprising an indication face portion on both sides of said palm portion.

5. A hand simulator as set forth in claim 1, wherein five holes are provided in said palm portion corresponding to said five finger portions, respectively.

6. A hand simulator as set forth in claim 5, wherein each of said holes is slightly smaller than the corresponding finger tip to establish a resilient resistance to removal of the corresponding finger tip.

7. A hand simulator as set forth in claim 1, wherein said palm and finger portions are formed from a foamed urethane product.

8. A hand simulator as set forth in claim 1 wherein each of said finger portions has sufficient resilience when bent and the finger tip inserted in a hole to regain an erect position extending from the palm portion upon the finger tip being pulled from the hole.

9. A hand simulator as set forth in claim 1, wherein said palm and finger portions are made from a single thickness cushiony material.

* * * * *